(12) United States Patent
Chou

(10) Patent No.: US 7,094,771 B2
(45) Date of Patent: Aug. 22, 2006

(54) PHARMACEUTICAL COMPOSITION FOR BORON NEUTRON CAPTURE THERAPY CONTAINING TRIPHENYLBOROXIN

(75) Inventor: Fong-In Chou, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 746 days.

(21) Appl. No.: 10/194,213

(22) Filed: Jul. 15, 2002

(65) Prior Publication Data

US 2004/0009954 A1    Jan. 15, 2004

(51) Int. Cl.
*A01N 43/04* (2006.01)
*A61K 31/70* (2006.01)

(52) U.S. Cl. ............ 514/64; 424/1.11; 424/1.21; 424/450

(58) Field of Classification Search ............ None
See application file for complete search history.

(56) References Cited

U.S. PATENT DOCUMENTS

| | | | | |
|---|---|---|---|---|
| 3,864,380 A | * | 2/1975 | King et al. | 558/338 |
| 5,641,793 A | * | 6/1997 | Bradbury | 514/352 |
| 5,861,401 A | * | 1/1999 | Bradbury | 514/255.05 |
| 6,083,951 A | * | 7/2000 | Bradbury | 514/256 |
| 6,117,852 A | | 9/2000 | Chou | 514/64 |

FOREIGN PATENT DOCUMENTS

JP        20020047292   *  2/2002

OTHER PUBLICATIONS

Mishima et al. Treatment of malignant melanoma by single thermal neutron capture therpy with melanoma seeking 10-B compound. Lancet. Aug. 12, 1989, vol. 2(8659), pp. 388-389.*

Hatanaka et al. International Journal of Radiation Oncology, Biology, Physics. vol. 28, pp. 1061-1066, 1994.*

Gravel et al., Universal Solid-Phase Approach for the Immodiblization, Derivatization, and Resin-to-Resin Transfer Reactions of Boronic Acids. Journal of Organic Chemistry. Published on Web: Nov. 29, 2001, 2002, vol. 67, pp. 3-15.*

Cited by Applicants in specification.*

Hawthorne et al. Preparation of Tumor-Specific Boron Compounds. 1. In vitro studies using boron-labeled antibodies and elemental boron as neutron targets. Journal of Medicinal Chemistry. May 1972, vol. 15, No. 5. pp. 449-452.*

Yanagie et al. Applied Radiation and Isotopes 61, pp. 639-646, 2004.*

Borkovec et al. J. Econ. Entomol. vol. 62(6), pp. 1472-1480, Dec. 1969.*

Robinson et al. Acta Cryst. C52, pp. 2826-2830, 1996.*

Mehta et al. Phar. Res, vol. 13, No. 3, pp. 344-351, 1996.*

Minoru Suzuki et al., "The Effects of Boron Neutron Capture Therapy on Liver Tumors and Normal Hepatocytes in Mice", Oct. 2000, pp. 1058-1064, Jpn. J. Cancer Res. 91.

Carolyn Bratt Brock, Robin P. Minton and Kurt Niedenzu, "Structure and Thermal Motion of Tripheynlboroxin", pp. 1775-1779, Acta Cryst. (1987). C43.

Barth, R.F., et al., "Boron Neutron Capture Therpay of Brain Tumors: Enhanced Survival and Cure Following Blood-Brain Barrier Disruption and Intracarotid Injection of sodium Borocaptate and Boronophenylalanine", 2000. pp. 209-218, Int. J. Radiation Oncology Biol. Phys. vol. 47, No. 1.

* cited by examiner

*Primary Examiner*—Janet L. Epps-Ford
(74) *Attorney, Agent, or Firm*—Bacon & Thomas, PLLC

(57) ABSTRACT

A pharmaceutical composition for boron neutron capture therapy (BNCT), and in particular for BNCT on hepatoma is disclosed. The pharmaceutical composition contains a therapeutically effective amount of triphenylboroxin (phenylboronic anhydride) as a boron source and a pharmaceutically acceptable carrier, such as lipiodol.

11 Claims, No Drawings

PHARMACEUTICAL COMPOSITION FOR BORON NEUTRON CAPTURE THERAPY CONTAINING TRIPHENYLBOROXIN

FIELD OF THE INVENTION

The present invention is related to a pharmaceutical composition for boron neutron capture therapy (herein after abbreviated as BNCT), and in particular to a pharmaceutical composition for BNCT containing triphenylboroxin as a boron source.

BACKGROUND OF THE INVENTION

In U.S. Pat. No. 6,117,852, the inventor of the present invention discloses a boron-containing lipiodol pharmaceutical composition comprising lipiodol, submicron boron powder, lecithin and $C_{12}$–$C_{22}$ fatty acid, wherein said submicron boron powder is suspended in said lipiodol in the presence of said lecithin and said $C_{12}$–$C_{22}$ fatty acid such as linoleic acid. This B-lipiodol pharmaceutical composition is at least useful in boron neutron capture therapy (BNCT) of hepatoma, wherein the lipiodol has a property of a high retention in hepatoma, the lecithin has a boron carrying capacity, and the $C_{12}$–$C_{22}$ fatty acid has a function of rendering lecithin soluble in lipiodol. In this B-lipiodol pharmaceutical composition the submicron boron powder must have an appropriate distribution of particle sizes in order to be uniformly dispersed therein. Details of U.S. Pat. No. 6,117,852 are incorporated herein by reference.

Using BSH (borocaptate sodium) and BPA (boronophenylalanine) in clinical trails for treatment of malignant melanoma and brain tumor has been reported [Mishima, Y., et al. Lancet, 12, 388–389 (1989); Hatanaka, H. and Nakagawa, Y. Int. J. Radiat. Oncol. Biol. Phys., 28, 1061–1066 (1994); Barth, R. F., et al. Int. J. Radiation Oncology Biol. Phys. Vol. 47, No. 1, 209–218 (2000)]. Further, Minoru Suzuki et al. have studied the effects of boron neutron capture therapy on liver tumors and normal hepatocytes in mice [Minoru Suzuki, et al., Jpn. J. Cancer Res. 91. 1058–1064, October 2000].

Carolyn Pratt Brock, Robin P. Minton and Kurt Niedenzu published an article in 1987 related to the structure and thermal motion of triphenylboroxin [Acta Cryst. (1987). C43, 1775–1779].

SUMMARY OF THE INVENTION

A primary objective of the present invention is to provide a boron-containing drug, which has a selectively high retention in cancer cells to be used as a boron source in the boron neutron capture therapy (BNCT).

Another objective of the present invention is to provide a pharmaceutical composition for boron neutron capture therapy (BNCT), which has the following advantages: a compound as a boron source in the pharmaceutical composition is able to be uniformly and stably dispersed in the pharmaceutical composition; the pharmaceutical composition is stable in serum; and the pharmaceutical composition can be selectively accumulated in cancer cells with a high concentration, as well as the boron-source compound.

In order to accomplish the objectives of the present invention, a pharmaceutical composition for BNCT prepared according to the present invention comprises a therapeutically effective amount of triphenylboroxin having the following formula (I) as a boron source and a pharmaceutically acceptable carrier, such as lipiodol:

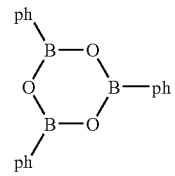

wherein ph is phenyl.

The pharmaceutical composition of the present invention is useful for BNCT on a cancer, for examples hepatoma, breast cancer and malignant melanoma.

Preferably, the pharmaceutical composition of the present invention further comprises a promoter for enhancing uptake of said carrier by the cancer cell.

Preferably, the pharmaceutical composition of the present invention further comprises a dissolving agent for enhancing said promoter's solubility in said carrier.

Preferably, said promoter is lecithin and said dissolving agent is C10–C20 fatty acid.

Preferably, the pharmaceutical composition of the present invention comprises 0.1% to 3% boron, based on the weight of the pharmaceutical composition.

Preferably, the pharmaceutical composition of the present invention comprises 15–25 mg lecithin and 0.05–0.09 ml C10–C20 fatty acid per ml of the lipiodol. More preferably, said C10–C20 fatty acid is linoleic acid.

DETAILED DESCRIPTION OF THE INVENTION

The inventor of the present application synthesizes a hydrophobic compound, triphenylboroxin ($C_{18}H_{15}B_3O_3$), having the following structure (I), and is the first person using it as a boron-containing drug in BNCT:

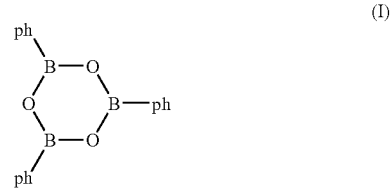

wherein ph is phenyl.

Lipiodol has been used as X-ray contrast medium and lymphography contrast medium. The present inventor and her co-workers in their previously study clearly demonstrated that hepatoma cells in culture are capable of rapidly active uptake of a large quantity of lipiodol by endocytosis with prolonged retention of the lipiodol intracellularly as long as the life span of the cells [Chou F I, Fang K C, Chung C, Lui W Y, Chi C W, Liu R S, and Chan W K. Lipiodol uptake and retention by human hepatoma cells. Nucl Med Biol (1995) 22(3): 379–386]. In this invention, the present inventor employs lipiodol as a boron-containing drug carrier in view of its capability of achieving selective and high retention in hepatoma cells. It is found that triphenylboroxin as the boron-containing drug has a property of uniform dispersion in lipiodol and is stable in lipiodol. This inventor further utilizes lecithin to enhance uptake of lipiodol by hepatoma cells, and linoleic acid to increase the solubility of lecithin in lipiodol. As a result, the pharmaceutical composition prepared in the present invention is suitable for use in BNCT on hepatoma. It is apparent that the pharmaceutical composition prepared in the present invention has a great potential for use in BNCT on other cancers such as breast cancer or malignant melanoma.

PREPARATION EXAMPLE

Synthesis of Triphenylboroxin (I)

To a round-bottom flask 3 g of phenylboronic acid and 1 ml of ethanolamine catalyst were added, and the mixture was heated with an oil bath at 130° C. for 24 hours while stirring by a magnetic stirrer. A red-brown solution was thus obtained. A portion of the red-brown solution was taken for thin-layer chromatography analysis (TLC), wherein a mixed solvent of hexane and ethyl acetate (hexane:ethyl acetate=5:2, V/V) was used as a mobile phase to develop the solution drop. After the silica gel TLC film being colored by $I_2$ vapor, a dark point was found at Rf of 0.5.

In order to remove the remaining ethanolamine, the red-brown solution was introduced into a column packed with aluminum oxide, and eluted with ethyl acetate (eluent). The eluate collected in the beginning section, after the solvent therein being evaporated, was subjected to another elution in a column packed with silica gel by using a mixed solvent of hexane and ethyl acetate (hexane:ethyl acetate=8:1, V/V) as an eluent. The eluate was collected in consecutive separate portions, each of which was dropped on a silica gel TLC film and developed by a mixed solvent of hexane and ethyl acetate (hexane:ethyl acetate=5:2, V/V) for carrying out TLC analysis. The silica gel TLC films were colored by $I_2$ vapor, and the one with a Rf of 0.5 was the target. The collected eluate portion having Rf of 0.5 was evaporated in vacuo to remove solvents contained therein, and a liquid product having hydrophobic triphenylboroxin as a major portion was obtained.

Identification of the Structure and Molecular Weight of Triphenylboroxin:

The liquid product purified by the aforesaid liquid chromatography was dropped on a thick silica gel TLC film (2 mm), and developed with a mixed solvent of hexane and ethyl acetate (hexane:ethyl acetate=5:2, V/V). The product at Rf of 0.5 was scrapped. The resulting powder was placed in a tube and dissolved by ethyl acetate. The solution was subjected to gas chromatography-mass spectrum (GC-MS) analysis, where a major product having a molecular weight of 312 was observed.

α Track of Triphenylboroxin After Neutron Irradiation:

5 µl of the triphenylboroxin liquid product prepared above was dropped on an α track detectable film (Koda, LR-115 film). After being allowed to dry overnight, the film was placed in Tsing Hua Open-pool Reactor (THOR), where it was irradiated by a thermal neutron beam for a predetermined period of time. The irradiated film was removed from the THOR, and developed by etching in 10% NaOH aqueous solution at 60° C. with sonication for 50 minutes. The etched film was washed with distilled water to remove residual NaOH, dried, and observed with phase-contrast microscope. α tracks were found in the area of the drop of the triphenylboroxin liquid product on the developed film.

EXAMPLE

Preparation of Triphenylboroxin Entrapped Lipiodol (Herein After Abbreviated as TEL)

To lipiodol, linoleic acid and lecithin in a round-bottom, anhydrous ethanol was added, and then heated at 70° C. for 20 minutes while stirring. Until the solution became completely clear, the triphenylboroxin liquid product prepared in Preparation Example was added, and the stirring and heating was maintained for another 10 minutes. The resulting mixture was placed in a rotary evaporator at 50° C. to remove the ethanol therefrom thoroughly, so that a triphenylboroxin entrapped lipiodol (TEL) was obtained in the form of an oily light yellow-brown clear liquid. An appropriate ratio of the components for preparing TEL was: triphenylboroxin liquid product:lipiodol:lecithin:linoleic acid:anhydrous ethanol=0.03ml:1 ml:20 mg:0.06 ml:about 30 ml.

α Track of TEL After Neutron Irradiation:

The procedures of α track of triphenylboroxin after neutron irradiation in Preparation Example were repeated except that the triphenylboroxin liquid product was replaced by TEL. The observation results of the developed film show that there are α tracks uniformly distributed in the area of the drop of TEL on the developed film, and no α track found outside the drop.

Boron Concentration of TEL:

To a Teflon® high pressure digestion vessel 0.5 ml of TEL, 3 ml of nitric acid solution (14 N, 65%) and 0.5 ml of hydrogen peroxide solution (30–35%) were added. The vessel was sealed with a cap and placed in a microwave digestion oven (MLS 1200 Miesfone, Italia) for the following digestions: 300 W for 15 minutes and 600 W for 10 minutes. After cooling for 60 minutes to reduce pressure in the vessel, the cap was turned off and the mixture in the vessel became a clear solution indicating a complete digestion. The digested solution was pour out, diluted with distill water, and assayed by inductively coupled plasma-atomic spectroscopy (ICP-AES, OPTIMA 2000 DV, Perkin Elmer Instruments). The boron content of TEL is 12000 ppm. The boron content of TEL varies with the formulation of preparing TEL. An appropriate range of the boron concentration based on the weight of TEL is from $1\times10^3$ ppm to $3\times10^4$ ppm.

The Stability of TEL:

For testing the stability of TEL in human serum, 0.1 ml of B-lipiodol having 12000 ppm boron was mixed with 5 mL human serum, and then incubated at 37° C. under 75 rpm to form a suspension of TEL vesicles in the serum. For quantitatively testing the release of boron from the oily preparation into the aqueous serum, 2 ml of serum was regularly sampled from each test tube which was maintained at 37° C. and rotated with 75 rpm. The boron contents of the samples were measured by ICP-AES, and the results show that the boron content of the TEL vesicles gradually reduced to 88% in the first four hours and stabilized thereafter, and 85% of the boron content was still retained in the TEL vesicles after 96 hours, indicating that triphenylboroxin was stably retain in lipiodol.

Interaction and Retention of TEL by HepG2 Cells 0.15 mL of TEL was added to 100 mL of the complete Dulbecco's Modified Eagle Medium (CDMEM), and then homogenized by sonication of 75 W power under sterile condition so that a TEL-CDMEM liquid was formed. 7 mL of the TEL-CDMEM was added to HepG2 cells which were cultured in CDMEM to 70% confluence, and the absolute boron content in the culture after the addition was 16 µg. When HepG2 cells were incubated with TEL-CDMEM, TEL globules were detected on the cell membrane by inverted light microscopic examination. After 1 h, the TEL on the cell membrane was found to be emulsified to form smaller globules. After 8 h of incubation with TEL-CMEM, most of the HepG2 cells had intracellular TEL globules in the cytoplasm, as confirmed by inverted light microscope. The intracellular B-lipiodol globules appeared to be larger in size and quantity as time increased. By 48 h, large numbers of TEL globules accumulated in the cytoplasm, causing the cell size to enlarge and the plasma membrane to bulge.

7 mL of the TEL-CDMEM was added to HepG2 cells which were cultured in CDMEM to 70% confluence, and the absolute boron content in the culture after the addition was 16 μg. After exposing of the HepG2 cells to TEL-CDMEM for predetermined periods of time, cells were washed twice with 5 ml of phosphate buffer (pH 7.4) to remove any loosely attached TEL. Cell were collected by centrifugation, and digested. The boron contents of the collected and digested cells were assayed by ICP-AES. The results reveal that the boron content of the collected and digested cells increase as the culture time of TEL-CDMEM increases, the boron contents at the culture time of 12 and 24 hours are 58 and 118 ppm respectively, and by 48 hours it reaches 214 ppm, which is sufficient high for BNCT.

The invention claimed is:

1. A pharmaceutical composition for boron neutron capture therapy comprising a therapeutically effective amount of triphenylboroxin having the following formula (I) as a boron source and a pharmaceutically acceptable carrier:

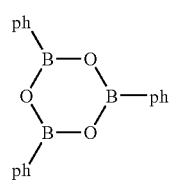

(I)

wherein ph is phenyl.

2. The pharmaceutical composition according to claim 1, which is for boron neutron capture therapy on a cancer.

3. The pharmaceutical composition according to claim 1, wherein said cancer is hepatoma, breast cancer or malignant melanoma.

4. The pharmaceutical composition according to claim 3, which said cancer is hepatoma.

5. The pharmaceutical composition according to claim 1, wherein said pharmaceutically acceptable carrier comprises lipiodol.

6. The pharmaceutical composition according to claim 1 further comprises a promoter for enhancing uptake of said pharmaceutically acceptable carrier by cancer cells.

7. The pharmaceutical composition according to claim 6 further comprises a dissolving agent for enhancing said promoter's solubility in said pharmaceutically acceptable carrier.

8. The pharmaceutical composition according to claim 7, wherein said promoter is lecithin and said dissolving agent is C10–C20 fatty acid.

9. The pharmaceutical composition according to claim 1, which comprises 0.1% to 3% boron, based on the weight of the pharmaceutical composition.

10. The pharmaceutical composition according to claim 8, which comprises 15–25 mg lecithin and 0.05–0.09 ml C10–C20 fatty acid per ml of the lipiodol; and 0.1% to 3% boron, based on the weight of the pharmaceutical composition.

11. The pharmaceutical composition according to claim 8, wherein said C10–C20 fatty acid is linoleic acid.

* * * * *